United States Patent [19]
Feuerstein

[11] Patent Number: 6,096,739
[45] Date of Patent: Aug. 1, 2000

[54] TREATMENT FOR CNS INJURIES

[75] Inventor: Giora Z. Feuerstein, Wynnewood, Pa.

[73] Assignee: SmithKline Beecham Corporation, Philadelphia, Pa.

[21] Appl. No.: 09/142,877

[22] PCT Filed: Mar. 24, 1997

[86] PCT No.: PCT/US97/05820

§ 371 Date: Sep. 18, 1998

§ 102(e) Date: Sep. 18, 1998

[87] PCT Pub. No.: WO97/35856

PCT Pub. Date: Oct. 2, 1997

Related U.S. Application Data

[60] Provisional application No. 60/014,137, Mar. 25, 1996.

[51] Int. Cl.$^7$ ............... A61K 31/4709; A61K 31/5377; A61P 25/00
[52] U.S. Cl. ........................... 514/235.2; 514/235.8; 514/272; 514/274; 514/318; 514/341
[58] Field of Search .................. 514/235.8, 235.2, 514/272

[56] References Cited

U.S. PATENT DOCUMENTS

| | | |
|---|---|---|
| 3,707,475 | 12/1972 | Lombardino . |
| 3,772,441 | 11/1973 | Lombardino . |
| 3,929,807 | 12/1975 | Fitzi . |
| 3,940,486 | 2/1976 | Fitzi . |
| 4,058,614 | 11/1977 | Baldwin . |
| 4,199,592 | 4/1980 | Cherkofsky . |
| 4,447,431 | 5/1984 | Sallmann . |
| 4,503,065 | 3/1985 | Wilkerson . |
| 4,565,875 | 1/1986 | Cavender . |
| 4,686,231 | 8/1987 | Bender et al. . |
| 4,822,805 | 4/1989 | Tasasugi et al. . |
| 5,656,644 | 8/1997 | Adams et al. . |
| 5,658,903 | 8/1997 | Adams et al. . |
| 5,663,334 | 9/1997 | Sheldrake et al. . |
| 5,670,527 | 9/1997 | Adams et al. . |
| 5,686,455 | 11/1997 | Adams et al. . |
| 5,739,143 | 4/1998 | Adams et al. . |

FOREIGN PATENT DOCUMENTS

| | | |
|---|---|---|
| WO92/10190 | of 1992 | WIPO . |
| WO92/10498 | of 1992 | WIPO . |
| WO 95/09847 | of 1995 | WIPO . |
| WO 95/09851 | of 1995 | WIPO . |
| WO 95/09852 | of 1995 | WIPO . |
| WO 95/09853 | of 1995 | WIPO . |
| WO95/02591 | of 1995 | WIPO . |
| WO96/21452 | of 1996 | WIPO . |
| WO96/21654 | of 1996 | WIPO . |
| WO96/40143 | of 1996 | WIPO . |
| WO97/25045 | of 1997 | WIPO . |
| WO97/25046 | of 1997 | WIPO . |
| WO97/25047 | of 1997 | WIPO . |
| WO97/25048 | of 1997 | WIPO . |
| WO97/35855 | of 1997 | WIPO . |
| WO97/35856 | of 1997 | WIPO . |
| WO98/22109 | of 1998 | WIPO . |

OTHER PUBLICATIONS

Dinarello et al., Rev.Infect.Disease, 6, p. 51 (1984).
Dinarello, J.Clin.Immun., 5(5), pp. 287–297 (1985).
Poli et al., Proc.Nat'l Acad.Sci., 87, pp. 782–784 (1990).
Kawasaki et al., J. Bio. Chem., 272(30), pp. 18518–18521.

*Primary Examiner*—Robert W. Ramsuer
*Attorney, Agent, or Firm*—Dara L. Dinner; Stephen Venetianer; Charles M. Kinzig

[57] ABSTRACT

Use of 1,4,5-substituted imidazole compounds and compositions in the treatment of CNS injuries to the brain.

11 Claims, No Drawings

TREATMENT FOR CNS INJURIES

This application is the §371 National Stage entery of PCT/US97/05820, filed Mar. 24, 1997 which claims the benefit of priority from provisional application US Ser. No. 60/014,137 filed Mar. 25, 1996.

FIELD OF THE INVENTION

This invention relates to a novel use of imidazole compounds in the treatment of CNS injuries.

BACKGROUND OF THE INVENTION

Interleukin-1 (IL-1) and Tumor Necrosis Factor (TNF) are biological substances produced by a variety of cells, such as monocytes or macrophages. IL-1 has been demonstrated to mediate a variety of biological activities thought to be important in immunoregulation and other physiological conditions such as inflammation [See, e.g., Dinarello et al., *Rev. Infect. Disease*, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis, and acute synovitis. Recent evidence also links IL-1 activity to diabetes and pancreatic β cells.

Dinarello, *J. Clinical Immunology*, 5 (5), 287–297 (1985), reviews the biological activities which have been attributed to IL-1. It should be noted that some of these effects have been described by others as indirect effects of IL-1.

Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, such as influenza, cachexia secondary to infection or malignancy, cachexia, secondary to acquired immune deficiency syndrome (AIDS), AIDS, ARC (AIDS related complex), keloid formation, scar tissue formation, Crohn's disease, ulcerative colitis, or pyresis.

Interleukin-8 (IL-8) is a chemotactic factor first identified and characterized in 1987. IL-8 is produced by several cell types including mononuclear cells, fibroblasts, endothelial cells, and keratinocytes. Its production from endothelial cells is induced by IL-1, TNF, or lipopolysachharide (LPS). Human IL-8 has been shown to act on Mouse, Guinea Pig, Rat, and Rabbit Neutrophils. Many different names have been applied to IL-8, such as neutrophil attractantlactivation protein-1 (NAP-1), monocyte derived neutrophil chemotactic factor (MDNCF), neutrophil activating factor (NAF), and T-cell lymphocyte chemotactic factor.

IL-8 stimulates a number of functions in vitro. It has been shown to have chemoattractant properties for neutrophils, T-lymphocytes, and basophils. In addition it induces histamine release from basophils from both normal and atopic individuals as well as lysozomal enzyme release and respiratory burst from neutrophils. IL-8 has also been shown to increase the surface expression of Mac-1 (CD11b/CD18) on neutrophils without de novo protein synthesis, this may contribute to increased adhesion of the neutrophils to vascular endothelial cells. Many diseases are characterized by massive neutrophil infiltration.

IL-1 and TNF affect a wide variety of cells and tissues and these cytokines as well as other leukocyte derived cytokines are important and critical inflammatory mediators of a wide variety of disease states and conditions. The inhibition of these cytokines is of benefit in controlling, reducing and alleviating many of these disease states.

There remains a need for the treatment, and for the prevention of CNS injuries which are related to the ability of compounds which are cytokine suppressive, i.e. compounds which are capable of inhibiting cytokines, such as IL-1, IL-6, IL-8 and TNF.

SUMMARY OF THE INVENTION

This invention relates to the use of CSAID™ cytokine suppressive binding compounds, or pharmaceutical compositions thereof in the treatment of CNS injuries, such as head trauma, and ischemia.

The preferred compounds for use as cytokine inhibitors are those compounds of Formula (I) as noted herein. The preferred method of inhibition is the inhibition of the CSBP/p38/RK kinase pathway.

DETAILED DESCRIPTION OF THE INVENTION

The present invention is to the novel use of a cytokine inhibitor, in particular that of cytokine CSBP/p38, for treating, in an acute setting, as well as preventing, in those individuals deemed susceptible to, various CNS injuries. A preferred group of these cytokine suppressive compounds are described herein as compounds of Formula (I).

CNS injuries as defined herein include both open or penetrating head trauma, such as by surgery, or a closed head trauma injury, such as by an injury to the head region. Also included within this definition is ischemic stroke, particularly to the brain area.

Ischemic stroke may be defined as a focal neurologic disorder that results from insufficient blood supply to a particular brain area, usually as a consequence of an embolus, thrombi, or local atheromatous closure of the blood vessel. The role of inflammatory cytokines in this are has been emerging and the present invention provides a mean for the potential treatment of these injuries. Relatively little treatment, for an acute injury such as these has been available.

TNF-α is a cytokine with proinflammatory actions, including endothelial leukocyte adhesion molecule expression. Leukocytes infiltrate into ischemic brain lesions and hence compounds which inhibit or decrease levels of TNF would be useful for treatment of ischemic brain injury. See Liu et al., Stoke, Vol. 25., No. 7, pp 1481–88 (1994) whose disclosure is incorporated herein by reference.

Models of closed head injuries and treatment with mixed 5-LO/CO agents is discussed in Shohami et al., J. of Vaisc & Clinical Physiology and Pharrnacology, Vol. 3, No. 2, pp 99–107 (1992) whose disclosure is incorporated herein by reference. Treatment which reduced edema formation was found to improve functional outcome in those animals treated.

Compounds for use herein include the cytokine inhibitors as described in US Ser. No. 08/091,491, published as WO95/02575; WO96/21452; US Ser. No. 08/369,964; US Ser. No. 08/473,396; US Ser. No. 08/659,102; US Ser. No. 08/764,003; WO96/40143; US Ser. No. 08/473,398; WO96/21654; WO93/14081; US Ser. No. 08/095,234; WO95/03297; US Ser. No. 08/481,671; PCT/US97/00619; PCT/US97/00614; PCT/US97/00500; PCT/US97/00529; US Ser. No. 60/013,357; US Ser. No. 60/013,358; US Ser. No. 60/013,359; WO93/14082; WO95/13067; and WO95/31451. Each of these references are incorporated by reference herein in their entirety.

Preferred compounds for use as cytokine inhibitors are those compounds of Formula (I) noted below. Synthetic chemistry and methods of pharmaceutical formulations thereof are also contained within each noted patent application. A description of the assay for inhibition of the cytokine specific binding protein (CSBP) is also found in WO95/07922, whose disclosure is incorporated by reference in its entirety.

Accordingly, the present invention provides for use of a compound of Formula (I):

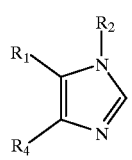

(I)

wherein:

$R_1$ is 4-pyridyl, pyrimidinyl, quinolyl, isoquinolinyl, quinazolin-4-yl, 1-imidazolyl or 1-benzimidazolyl, which heteroaryl ring is optionally substituted independently one to three times with Y, $NHR_a$, optionally substituted $C_{1-4}$ alkyl, halogen, hydroxyl, optionally substituted $C_{1-4}$ alkoxy, optionally substituted $C_{1-4}$ alkylthio, $C_{1-4}$ alkylsulfmyl, $CH_2OR_{12}$, amino, mono and di- $C_{1-6}$ alkyl substituted amino, or $N(R_{10})C(O)R_b$;

Y is $X_1$—$R_a$;

$X_1$ is oxygen or sulfur;

$R_4$ is phenyl, naphth-1-yl or naphth-2-yl, or a heteroaryl, which is optionally substituted by one or two substituents, each of which is independently selected, and which, for a 4-phenyl, 4-naphth-1-yl, 5-naphth-2-yl or 6-naphth-2-yl substituent, is halogen, cyano, nitro, —$C(Z)NR_7R_{17}$, —$C(Z)OR_{16}$, —$(CR_{10}R_{20})_vCOR_{12}$, —$SR_5$, —$SOR_5$, —$OR_{12}$, halo-substituted-$C_{1-4}$ alkyl, $C_{1-4}$ alkyl, —$ZC(Z)R_{12}$, —$NR_{10}C(Z)R_{16}$, or —$(CR_{10}R_{20})_vNR_{10}R_{20}$ and which, for other positions of substitution, is halogen, cyano, —$C(Z)NR_{13}R_{14}$, —$C(Z)OR_3$, —$(CR_{10}R_{20})_{m"}COR_3$, —$S(O)_mR_3$, —$OR_3$, halo-substituted-$C_{1-4}$ alkyl, —$C_{1-4}$ alkyl, —$(CR_{10}R_{20})_{m"}NR_{10}C(Z)R_3$, —$NR_{10}S(O)_{m'}R_8$, —$NR_{10}S(O)_{m'}NR_7R_{17}$, —$ZC(Z)R_3$ or —$(CR_{10}R_{20})_{m"}NR_{13}R_{14}$;

v is 0, or an integer having a value of 1 or 2;

m is 0, or the integer 1 or 2;

m' is an integer having a value of 1 or 2, m" is 0, or an integer having a value of 1 to 5;

$R_2$ is $C_{1-10}$ alkyl $N_3$, —$(CR_{10}R_{20})_{n'}OR_9$, heterocyclyl, heterocyclyl$C_{1-10}$ alkyl, $C_{1-10}$alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$ cycloalkenyl $C_{1-10}$alkyl, aryl, aryl$C_{1-10}$ alkyl, heteroaryl, heteroaryl $C_{1-10}$alkyl, $(CR_{10}R_{20})_nOR_{11}$, $(CR_{10}R_{20})_nS(O)_mR_{18}$, $(CR_{10}R_{20})_nNHS(O)2R_{18}$, $(CR_{10}R_{20})_nNR_{13}R_{14}$, $(CR_{10}R_{20})_nNO_2$, $(CR_{10}R_{20})_nCN$, $(CR_{10}R_{20})_{n'}SO_2R_{18}$, $(CR_{10}R_{20})_nS(O)_{m'}NR_{13}R_{14}$, $(CR_{10}R_{20})_nC(Z)R_{11}$, $(CR_{10}R_{20})_nOC(Z)R_{11}$, $(CR_{10}R_{20})_nC(Z)OR_{11}$, $(CR_{10}R_{20})_nC(Z)NR_{13}R_{14}$, $(CR_{10}R_{20})_nC(Z)NR_{11}OR_9$, $(CR_{10}R_{20})_nNR_{10}C(Z)R_{11}$, $(CR_{10}R_{20})_nNR_{10}C(Z)NR_{13}R_{14}$, $(CR_{10}R_{20})_nN(OR_6)C(Z)NR_{13}R_{14}$, $(CR_{10}R_{20})_nN(OR_6)C(Z)R_{11}$, $(CR_{10}R_{20})_nC(=NOR_6)R_{11}$, $(CR_{10}R_{20})_nNR_{10}C(=NR_{19})NR_{13}R_{14}$, $(CR_{10}R_{20})_nOC(Z)NR_{13}R_{14}$, $(CR_{10}R_{20})_nNR_{10}C(Z)NR_{13}R_{14}$, $(CR_{10}R_{20})_nNR_{10}C(Z)OR_{10}$, 5-($R_{18}$)-1,2,4-oxadizaol-3-yl or 4-($R_{12}$)-5-($R_{18}R_{19}$)-4,5-dihydro-1,2,4-oxadiazol-3-yl; wherein the cycloalkyl, cycloalkylalkyl, aryl, arylalkyl, heteroaryl, heteroaryl alkyl, heterocyclic and heterocyclic alkyl groups may be optionally substituted;

n is an integer having a value of 1 to 10;

n' is 0, or an integer having a value of 1 to 10;

Z is oxygen or sulfur;

$R_a$ is $C_{1-6}$alkyl, aryl, aryl$C_{1-6}$alkyl, heterocyclic, heterocyclyl$C_{1-6}$ alkyl, heteroaryl, or heteroaryl$C_{1-6}$alkyl, wherein each of these moieties may be optionally substituted;

$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alyl;

$R_3$ is heterocyclyl, heterocyclyl$C_{1-10}$ alkyl or $R_8$;

$R_5$ is hydrogen, $C_{1-4}$ alkyl, $C_{2-4}$ alkenyl, $C_{2-4}$ alkynyl or $NR_7R_{17}$, excluding the moieties —$SR_5$ being —$SNR_7R_{17}$ and —$SOR_5$ being —$SOH$;

$R_6$ is hydrogen, a pharmaceutically acceptable cation, $C_{1-10}$ alkyl, $C_{3-7}$ cycloalkyl, aryl, aryl$C_{1-4}$ alkyl, heteroaryl, heteroaryl$C_{1-4}$ alkyl, heterocyclic, aroyl, or $C_{1-10}$ alkanoyl;

$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{15}$;

$R_8$ is $C_{1-10}$ alkyl, halo-substituted $C_{1-10}$ alkyl, $C_{2-10}$ alkenyl, $C_{2-10}$ alkynyl, $C_{3-7}$ cycloLkyl, $C_{5-7}$ cycloalkenyl, aryl, aryl$C_{1-10}$ alkyl, heteroaryl, heteroaryl$C_{1-10}$ alkyl, $(CR_{10}R_{20})_nOR_{11}$, $(CR_{10}R_{20})_nS(O)_mR_{18}$, $(CR_{10}R_{20})_nNHS(O)_2R_{18}$, $(CR_{10}R_{20})_nNR_{13}R_{14}$; wherein the aryl, arylalkyl, heteroaryl, heteroaryl alkyl may be optionally substituted;

$R_9$ is hydrogen, —$C(Z)R_{11}$ or optionally substituted $C_{1-10}$ alkyl, $S(O)_2R_{18}$, optionally substituted aryl or optionally substituted aryl-$C_{1-4}$ alkyl;

$R_{10}$ and $R_{20}$ is each independently selected from hydrogen or $C_{1-4}$ alkyl;

$R_{11}$ is hydrogen, $C_{1-10}$ alkyl, $C_{3-7}$ cycloalkyl, heterocyclyl, heterocyclyl $C_{1-10}$ alkyl, aryl, aryl$C_{1-10}$ alkyl, heteroaryl or heteroaryl$C_{1-10}$ alkyl;

$R_{12}$ is hydrogen or $R_{16}$;

$R_{13}$ and $R_{14}$ is each independently selected from hydrogen or optionally substituted $C_{1-4}$ alkyl, optionally substituted aryl or optionally substituted aryl-$C_{1-4}$ alkyl, or together with the nitrogen to which they are attached form a heterocyclic ring of 5 to 7 members which ring optionally contains an additional heteroatom selected from oxygen, sulfur or $NR_9$;

$R_{15}$ is $R_{10}$ or $C(Z)-C_{1-4}$ alkyl;

$R_{16}$ is $C_{1-4}$ alkyl, halo-substituted-$C_{1-4}$ alkyl, or $C_{3-7}$ cycloalkyl;

$R_{18}$ is $C_{1-10}$ alkyl, $C_{3-7}$ cycloalkyl, heterocyclyl, aryl, arylalkyl, heterocyclyl, heterocyclyl-$C_{1-10}$alkyl, heteroaryl or heteroarylalkyl;

$R_{19}$ is hydrogen, cyano, $C_{1-4}$ alkyl, $C_{3-7}$ cycloalkyl or aryl; or a pharmaceutically acceptable salt thereof.

Suitably, $R_1$ is 4-pyridyl, pyrimidinyl, quinolyl, isoquinolinyl, quinazolin-4-yl, 1-imidazolyl or 1-benzirnidazolyl. Preferably, $R_1$ is an optionally substituted 4-pyridyl or 4-pyrimindyl, more preferably an optionally substituted 4-pyrimidinyl.

The $R_1$ heteroaryl ring may be optionally substituted independently one to three times with Y, $NHR_a$, optionally substituted $C_{1-4}$ alkyl, halogen, hydroxyl, optionally substituted $C_{1-4}$ alkoxy, optionally substituted $C_{1-4}$ alkylthio, $C_{1-4}$ alkylsulfinyl, $CH_2OR_{12}$, amino, mono and di- $C_{1-6}$ alkyl substituted amino, or $N(R_{10})C(O)R_b$.

Suitably Y is $X_1-R_a$ wherein $X_1$ is oxygen or sulfur, preferably oxygen.

Preferably the hetoaryl ring $R_1$ is substituted by alkoxy, alkylthio, amino, methylamino, $NHR_a$, or Y. More preferably, Y, $NHR_a$, or $C_{1-4}$ alkoxy. A preferred ring placement of the $R_1$ substituent on the 4-pyridyl derivative is the 2-position, such as 2-methoxy-4-pyridyl. A preferred ring placement on the 4-pyrimidinyl ring is also at the 2-position, such as in 2-methoxy-pyrimidinyl.

Suitably, $R_a$ is $C_{1-6}$ alkyl, aryl, aryl$C_{1-6}$ alkyl, heterocyclic, heterocyclyl$C_{1-6}$ alkyl, heteroaryl, or heteroaryl$C_{1-6}$alkyl, wherein each of these moieties may be optionally substituted.

Suitably, $R_b$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl.

When the substituent is Y, and $R_a$ is aryl, it is preferably phenyl or naphthyl. When $R_a$ is aryl alkyl, it is preferably benzyl or napthylmethyl. When $R_a$ is heterocyclic or heterocyclic alkyl moiety, the heterocyclic portion is preferably pyrrolindinyl, piperidine, morpholino, tetrahydropyran, tetrahydrothiopyranyl, tetrahydrothipyran-sulfinyl, tetrahydrothio-pyransulfonyl, pyrrolindinyl, indole, or piperonyl. It is noted that the heterocyclic rings herein may contain unsaturation, such as in a tryptamine ring.

These $R_a$ aryl, heterocyclic and heteroaryl rings may also be optionally substituted one or more times independently with halogen; $C_{1-4}$ alkyl, such as methyl, ethyl, propyl, isopropyl, or t-butyl; halosubstituted alkyl, such as $CF_3$; hydroxy; hydroxy substituted $C_{1-4}$ alkyl; $C_{1-4}$ alkoxy, such as methoxy or ethoxy; $S(O)_m$alkyl and $S(O)m$ aryl (wherein m is 0, 1, or 2); $C(O)OR_{11}$, such as $C(O)C_{1-4}$ alkyl or C(O)OH moieties; $C(O)R_{11}$; —$OC(O)R_c$; O—$(CH_2)s$—O—, such as in a ketal or dioxyalkylene bridge; amino; mono- and di-$C_{1-6}$ alkylsubstituted amino; —$N(R_{10})C(O)$ $R_b$; —$C(O)NR_{10}R_{20}$; cyano, nitro, or an N-heterocyclyl ring which ring has from 5 to 7 members and optionally contains an additional heteroatom selected from oxygen, sulfur or $NR_{15}$; optionally subtituted aryl, such as phenyl; an optionally substituted arylalkyl, such as benzyl or phenethyl; aryloxy, such as phenoxy; or arylallyloxy such as benzyloxy; these aryl and arylalkyl moieties may be substituted with halogen, alkyl, alkoxy, S(O)m alkyl, amino, or mono- and di-$C_{1-6}$ alkylsubstituted amino.

Suitably $R_c$ is optionally substituted $C_{1-6}$ alkyl, $C_{3-7}$ cycloalkyl, aryl, aryl$C_{1-4}$ alkyl, heteroaryl, heteroaryl$C_{1-4}$ alkyl, heterocyclyl, or heterocyclyl$C_{1-4}$ alkyl moieties.

Preferably, the $R_a$ groups include benzyl, halosubstituted benzyl, napthylmethyl, phenyl, halosubstituted phenyl, aminocarbonylphenyl, alkylphenyl, cyanophenyl, alkylthiophenyl, hydroxyphenyl, alkoxyphenyl, morpholinopropyl, piperonyl, piperidin-4-yl, alkyl substituted piperidine, such as 1-methyl piperidine, or 2,2,6,6-tetramethylpiperidin-4-yl.

Preferably, when the substituent is $NHR_a$ then $R_a$ is aryl, arylalkyl, halosubstituted arylalkyl, halosubstituted aryl, heterocyclic alkyl, hydroxy alkyl, alkyl-1-piperidinecarboxylate, heterocyclic, alkyl substituted heterocyclic, halosubstituted heterocyclic, or aryl substituted heterocyclic. More specifically $R_a$ is benzyl, halosubstituted benzyl, napthylmethyl, phenyl, halosubstituted phenyl, morpholinopropyl, 2-hydroxy ethyl, ethyl-1-piperidinecarboxylate, piperonyl, piperidin-4-yl, alkyl substituted piperidine, chlorotryptamine, and tetrathiohydropyranyl.

Preferably, when the $R_1$ optionally substituent is a substituted $C_{1-4}$ alkoxy or $C_{1-4}$ alkylthio, the alkyl chain is substituted by halogen, such as fluorine, chlorine, bromine or iodine; hydroxy, such as hydroxyethoxy; $C_{1-10}$ alkoxy, such as a methoxymethoxy, S(O)m alkyl, wherein m is 0, 1 or 2; amino, mono & di-substituted amino, such as in the $NR_7R_{17}$ group, i.e. tert-butylaminoethoxy; or where the $R_7R_{17}$ may together with the nitrogen to which they are attached cyclize to form a 5 to 7 membered ring which optionally includes an additional heteroatom selected from O/N/S; $C_{1-10}$ alkyl, cycloalkyl, or cycloalkyl alkyl group, such as methyl, ethyl, propyl, isopropyl, t-butyl, etc. or cyclopropyl methyl; or halosubstituted $C_{1-10}$ alkyl, such as $CF_3$. Preferably, such $R_1$ substituents are tertbutylaminoethoxy, or hydroxyethoxy.

Preferably, the $R_4$ moiety is an unsubstituted or substituted phenyl moiety. More preferably, $R_4$ is phenyl or phenyl substituted at the 4-position with fluoro and/or substituted at the 3-position with fluoro, chloro, $C_{1-4}$ alkoxy, methanesulfonamido or acetamido, or $R_4$ is a phenyl di-substituted at the 3,4-position independently with chloro or fluoro, more preferably chloro. Most preferably, $R_4$ is 4-fluorophenyl.

In Formula (I), Z is suitably oxygen or sulfur.

Suitably, $R_2$ is selected from $C_{1-10}$ alkyl, optionally substituted heterocyclyl, optionally substituted heterocyclyl $C_{1-10}$ alkyl, $(CR_{10}R_{20})_nNS(O)_2R_{18}$, $(CR_{10}R_{20})_nS(O)_mR_{18}$, aryl$C_{1-10}$ alkyl, $(CR_{10}R_{20})_nNR_{13}R_{14}$, optionally substituted $C_{3-7}$cycloalkyl, or optionally substituted $C_{3-7}$cycloalkyl $C_{1-10}$ alkyl. Preferably $R_2$ is morpholino propyl, piperidine, N-methylpiperidine, N-benzylpiperidine, 2,2,6,6-tetramethylpiperidine, 4-aminopiperidine, 4-amino-2,2,6,6-tetramethyl piperidine, 4-hydroxycyclohexyl, 4-methyl-4-hydroxy cyclohexyl, 4-pyrrolinindyl-cyclohexyl, 4-methyl-4-aminocyclohexyl, 4-methyl-4-acetamidocyclohexyl, 4-keto cyclohexyl, 4-oxiranyl, or 4-hydroxy-4-( 1 -propynyl)cyclohexyl.

Preferably $R_2$ is an optionally substituted heterocyclyl ring, and optionally substituted heterocyclyl$C_{1-10}$ alkyl, an optionally substituted $C_{1-10}$ alkyl, an optionally substituted $C_{3-7}$cycloalkyl, an optionally substituted $C_{3-7}$cycloalkyl $C_{1-10}$ alkyl, $(CR_{10}R_{20})_nC(Z)OR_{11}$ group, $(CR_{10}R_{20})_n$ $NR_{13}R_{14}$, $(CR_{10}R_{20})_nNHS(O)_2R_{18}$, $(CR_{10}R_{20})_nS(O)_mR_{18}$, an optionally substituted aryl; an optionally substituted aryl$C_{1-10}$ alkyl, $(CR_{10}R_{20})_nOR_{11}$, $(CR_{10}R_{20})_nC(Z)R_{11}$, or $(CR_{10}R_{20})_nC(=NOR_6)R_{11}$ group.

More preferably $R_2$ is an optionally substituted heterocyclyl ring, and optionally substituted heterocyclyl$C_{1-10}$ alkyl, an optionally substituted $C_{3-7}$cycloalkyl, or an optionally substituted $C_{3-7}$cycloalkyl $C_{1-10}$ alkyl.

More preferably $R_2$ is an optionally substituted $C_4$ or $C_6$ cycloalkyl; morpholinyl butyl; morpholinyl propyl; morpholinyl ethyl; cyclohexyl substituted by methyl, phenyl, benzyl, amino, acetamide, aminomethyl, aminoethyl, cyanomethyl, cyanoethyl, hydroxy, nitroethyl, pyrrolidinyl, ethynyl, 1-propynyl, =O, O—(CH$_2$)$_2$O—, =NOR$_{11}$, wherein R$_{11}$ is hydrogen, alkyl or aryl, NHOH, or N(OH)—C(O)—NH$_2$; aminopropyl; piperidinyl; N-benzyl-4-piperidinyl; N-methyl4-piperidinyl; 2,2,6,6-tetramethypiperidinyl; substituted piperidine, such as 1-Formyl-4-piperidine; or a 1-ethoxycarbonyl-4-piperidine.

When $R_2$ is an optionally substituted heterocyclyl, the ring is preferably a morpholino, pyrrolidinyl, or a piperidinyl group. When the ring is optionally substituted, the substituents may be directly attached to the free nitrogen, such as in the piperidinyl group or pyrrole ring, or on the ring itself. Preferably the ring is a piperidine or pyrrole, more preferably piperidine. The heterocyclyl ring may be optionally substituted one to four times independently by halogen; $C_{1-4}$ alkyl; aryl, such as phenyl; aryl alkyl, such as benzyl and wherein the aryl or aryl alkyl moieties themselves may be optionally substituted (as in the definition section below); C(O)OR$_{11}$, such as the C(O)C$_{1-4}$ alkyl or C(O)OH moieties; C(O)H; C(O)C$_{1-4}$ alkyl, hydroxy substituted C$_{1-4}$ alkyl, C$_{1-4}$ alkoxy, S(O)$_m$C$_{1-4}$ alkyl (wherein m is 0, 1, or 2), NR$_{10}$R$_{20}$ (wherein R$_{10}$ and R$_{20}$ are independently hydrogen or C$_{1-4}$alkyl).

Preferably if the ring is a piperidine, the ring is attached to the imidazole at the 4-position, and the substituents are directly on the available nitrogen, i.e. a 1-Formyl-4-piperidine, 1-benzyl-4-piperidine, 1-methyl-4piperidine, 1-ethoxycarbonyl-4-piperidine. If the ring is substituted by an alkyl group and the ring is attached in the 4-position, it is preferably substituted in the 2- or 6- position or both, such as 2,2,6,6-tetramethyl-4-piperidine. Similarly, if the ring is a pyrrole, the ring is attached to the imidazole at the 3-position, and the substituents are all directly on the available nitrogen.

When $R_2$ is an optionally substituted heterocyclyl $C_{1-10}$ alkyl group, the ring is preferably a morpholino, pyrrolidinyl, or a piperidinyl group. Preferably this alkyl moiety is from 1 to 4, more preferably 3 or 4, and most preferably 3, such as in a propyl group. Preferred heterocyclic alkyl groups include but are not limited to, morpholino ethyl, morpholino propyl, pyrrolidinyl propyl, and piperidinyl propyl moieties. The heterocyclic ring herein is also optionally substituted in a similar mnanner to that indicated above for the direct attachment of the heterocyclyl.

When $R_2$ is an optionally substituted $C_{3-7}$cycloalkyl, or an optionally substituted $C_{3-7}$cycloalkyl $C_{1-10}$ alkyl, the cycloalkyl group is preferably a $C_4$ or $C_6$ ring, most preferably a $C_6$ ring, which ring is optionally substituted. The cycloalkyl ring may be optionally substituted one to three times independently by halogen, such as fluorine, chlorine, bromine or iodine; hydroxy; $C_{1-10}$ alkoxy, such as methoxy or ethoxy; S(O)$_m$ alkyl, wherein m is 0, 1, or 2, such as methyl thio, methylsulfinyl or methyl sulfonyl; S(O)$_m$ aryl; cyano, nitro, amino, mono & di-substituted amino, such as in the NR$_7$R$_{17}$ group, wherein R$_7$ and R$_{17}$ are as defined in Formula (I), or where the R$_7$R$_{17}$ may cyclize together with the nitrogen to which they are attached to form a 5 to 7 membered ring which optionally includes an additional heteroatom selected from oxygen, sulfur or NR$_{15}$ (and R$_{15}$ is as defined for Formula (I)); N(R$_{10}$)C(O)X'$_1$ (wherein R$_{10}$ is as defined in Formula (I)), and X'$_1$ is C$_{1-4}$ alkyl, aryl or arylC$_{1-4}$alkyl); N(R$_{10}$)C(O) aryl; C$_{1-10}$ alkyl, such as methyl, ethyl, propyl, isopropyl, or t-butyl; optionally substituted alkyl wherein the substituents are halogen, (such as CF$_3$), hydroxy, nitro, cyano, amino, mono & di-substituted amino, such as in the NR$_7$R$_{17}$ group, S(O)m alkyl and S(O)m aryl, wherein m is 0, 1 or 2; optionally substituted alkylene, such as ethylene or propylene; optionally substituted alkyne, such as ethyne; C(O)OR$_{11}$ (wherein R$_{11}$ is as defined in Formula (I)), such as the free acid or methyl ester derivative; the group R$_e$; —C(O)H; =O; =N—OR$_{11}$; —N(H)—OH (or substituted alkyl or aryl derivatives thereof on the nitrogen or the oxime moiety); —N(OR$_d$)—C(O)—R$_6$; an optionally substituted aryl, such as phenyl; an optionally substituted arylC$_{1-4}$alkyl, such as benzyl of phenethyl; an optionally substituted heterocycle or heterocyclic C$_{1-4}$alkyl, and further these aryl, arylalkyl, heterocyclic, and heterocyclic alkyl moieties are optionally substituted one to two times by halogen, hydroxy, C$_{1-10}$ alkoxy, S(O)m alkyl, cyano, nitro, amino, mono & di-substituted amino, such as in the NR$_7$R$_{17}$ group, an alkyl, halosubstituted alkyl.

Suitably R$_d$ is hydrogen, a pharmaceutically acceptable cation, aroyl or a C$_{1-10}$ alkanoyl group.

Suitably R$_e$ is a 1,3-dioxyalkylene group of the formula —O—(CH$_2$)$_s$—O—, wherein s is 1 to 3, preferably s is 2 yielding a 1,3-dioxyethylene moiety, or ketal functionality.

Suitably R$_6$ is NR$_{19'}$R$_{20'}$; alkyl $_{1-6}$; halosubstituted alkyl $_{1-6}$; hydroxy substituted alkyl $_{1-6}$; alkenyl $_{2-6}$; aryl or heteroaryl optionally substituted by halogen, alkyl $_{1-6}$, halosubstituted alkyl $_{1-6}$, hydroxyl, or alkoxy $_{1-6}$.

Suitably R$_{19'}$ is H or alkyl$_{1-6}$.

Suitably R$_{20'}$ is H, alkyl$_{1-6}$, aryl, benzyl, heteroaryl, alkyl substituted by halogen or hydroxyl, or phenyl substituted by a member selected from the group consisting of halo, cyano, alkyl$_{1-12}$, alkoxy $_{1-6}$, halosubstituted alkyl $_{1-6}$, alkylthio, alkylsulphonyl, or alkylsulfmyl; or R$_{19'}$and R$_{20'}$may together with the nitrogen to which they are attached form a ring having 5 to 7 members, which members may be optionally replaced by a heteroatom selected from oxygen, sulfur or nitrogen. The ring may be saturated or contain more than one unsaturated bond. Preferably R$_6$ is NR$_{19'}$R$_{20'}$and R$_{19'}$and R$_{20'}$are preferably hydrogen.

When the R$_2$ cycloalkyl moiety is substituted by NR$_7$R$_{17}$ group, or NR$_7$R$_{17}$ C$_{1-10}$ alkyl group, and the R$_7$ and R$_{17}$ are as defined in Formula (I), the substituent is preferably an amino, amino alkyl, or an optionally substituted pyrrolidinyl moiety.

A preferred ring placement on the cycloalkyl moiety is the 4-position, such as in a C$_6$ ring. When the cycloalkyl ring is di-substituted it is preferably di-substituted at the 4 position, such as in:

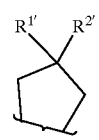

wherein R$^{1'}$ and R$^{2'}$ are independently the optional substituents indicated above for R$_2$. Preferably, R$^{1'}$ and R$^{2'}$ are hydrogen, hydroxy, alkyl, substituted alkyl, optionally substituted alkyne, aryl, arylalkyl, NR$_7$R$_{17}$, and N(R$_{10}$)C(O)R$_{11}$. Suitably, alkyl is C$_{1-4}$ alkyl, such as methyl, ethyl, or isopropyl; NR$_7$R$_{17}$ and NR$_7$R$_{17}$ alkyl, such as amino, methylarnino, arninomethyl, arninoethyl; substituted alkyl such as in cyanomethyl, cyanoethyl, nitroethyl, pyrrolidinyl; aryl such as in phenyl; arylalkyl, such as in benzyl; optionally substituted alkyne, such as ethyne or propynyl; or together R$^{1'}$ and R$^{2'}$ are a keto functionality.

In all instances herein where there is an alkenyl or alkynyl moiety as a substituent group, the unsaturated linkage, i.e., the vinylene or acetylene linkage is preferably not directly attached to the nitrogen, oxygen or sulfur moieties, for instance in $OR_3$, or for certain $R_2$ moieties.

As used herein, "optionally substituted", unless specifically defined, shall mean such groups as halogen, such as fluorine, chlorine, bromine or iodine; hydroxy; hydroxy substituted $C_{1-10}$alkyl; $C_{1-10}$ alkoxy, such as methoxy or ethoxy; S(O)m alkyl, wherein m is 0, 1 or 2, such as methyl thio, methylsulfinyl or methyl sulfonyl; amino, mono & di-substituted amino, such as in the $NR_7R_{17}$ group; or where the $R_7R_{17}$ may together with the nitrogen to which they are attached cyclize to form a 5 to 7 membered ring which optionally includes an additional heteroatom selected from O/N/S; $C_{1-10}$ alkyl, cycloalkyl, or cycloalkyl alkyl group, such as methyl, ethyl, propyl, isopropyl, t-butyl, etc. or cyclopropyl methyl; halosubstituted $C_{1-10}$ alkyl, such $CF_3$; halosubstituted $C_{1-10}$ alkoxy; an optionally substituted aryl, such as phenyl, or an optionally substituted arylalkyl, such as benzyl or phenethyl, wherein these aryl moieties may also be substituted one to two times by halogen; hydroxy; hydroxy substituted alkyl; $C_{1-10}$ alkoxy; $S(O)_m$ alkyl; amino, mono & di-substituted amino, such as in the $NR_7R_{17}$ group; alkyl, or $CF_3$.

Suitable pharmaceutically acceptable salts are well known to those skilled in the art and include basic salts of inorganic and organic acids, such as hydrochloric acid, hydrobromic acid, sulfuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of Formula (I) may also be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations.

The following terms, as used herein, refer to:

"halo" or "halogens", include the halogens: chloro, fluoro, bromo and iodo.

"$C_{1-10}$alkyl" or "alkyl"—both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

The term "cycloalkyl" is used herein to mean cyclic radicals, preferably of 3 to 8 carbons, including but not limited to cyclopropyl, cyclopentyl, cyclohexyl, and the like.

The term "cycloalkenyl" is used herein to mean cyclic radicals, preferably of 5 to 8 carbons, which have at least one bond including but not limited to cyclopentenyl, cyclohexenyl, and the like.

The term "alkenyl" is used herein at all occurrences to mean straight or branched chain radical of 2–10 carbon atoms, unless the chain length is limited thereto, including, but not limited to ethenyl, 1-propenyl, 2-propenyl, 2-methyl-1-propenyl, 1-butenyl, 2-butenyl and the like.

"aryl"—phenyl and naphthyl;

"heteroaryl" (on its own or in any combination, such as "heteroaryloxy", or "heteroaryl alkyl")—a 5–10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, thiazole, thiadiazole, triazole, imidazole, or benzimidazole.

"heterocyclic" (on its own or in any combination, such as "heterocyclylalkyl")—a saturated or partially unsaturated 4–10 membered ring system in which one or more rings contain one or more heteroatoms selected from the group consisting of N, O, or S; such as, but not limited to, pyrrolidine, piperidine, piperazine, morpholine, tetrahydro pyran, or imidazolidine.

The term "aralkyl" or "heteroarylalkyl" or "heterocyclicalkyl" is used herein to mean $C_{1-4}$ alkyl as defined above attached to an aryl, heteroaryl or heterocyclic moiety as also defined herein unless otherwise indicated.

"sulfinyl"—the oxide S (O) of the corresponding sulfide, the term "thio" refers to the sulfide, and the term "sulfonyl" refers to the fully oxidized $S(O)_2$ moiety.

"aroyl"—a C(O)Ar, wherein Ar is a phenyl, naphthyl, or aryl alkyl derivative such as defined above, such groups include but are not limited to benzyl and phenethyl.

"alkanoyl"—a $C(O)C_{1-10}$ alkyl wherein the alkyl is as defined above.

For the purposes herein the "core" 4-pyrimidinyl moiety for $R_1$ is referred to

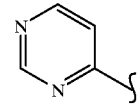

as the formula:

The compounds of the present invention may contain one or more asymunetric carbon atoms and may exist in racemic and optically active forms. All of these compounds are included within the scope of the present invention.

Exemplified compounds of Formula (I) include:

1-[3-(4-Morpholinyl)propyl]-4-(4-fluorophenyl)-5-(4-pyridyl)imidazole;

1-(3-Chloropropyl)-4-(4-fluorophenyl)-5-(4-pyridyl)imidazole;

1-(3-Azidopropyl)-4-(4-fluorophenyl)-5-(4-pyridyl)imidazole;

1-(3-Aminopropyl)-4-(4-fluorophenyl)-5-(4-pyridyl)imidazole;

1-(3-Methylsulfonamidopropyl)4(4-fluorophenyl)-5-(4-pyridyl)imidazole;

1-[3-(N-Phenylmethyl)aminopropyl]-4-(4-fluorophenyl)-5-(4-pyridyl)imidazole;

1-[3-(N-Phenylmethyl-N-methyl)aminopropyl]-4-(4-fluorophenyl)-5-(4-pyridyl)imidazole;

1-[3-(1-Pyrrolidinyl)propyl]-4-(4-fluorophenyl)-5-(4-pyridyl)imidazole;

1-(3-Diethylaminopropyl)4-(4-fluorophenyl)-5-(4-pyridyl)imidazole;

1-[3-(1-Piperidinyl)propyl]-4-(4-fluorophenyl)-5-(4-pyrdyl)imidazole;

1-[3-(Meth ylthio)propyl]-4-(4-fluorophenyl)-5-(4-pyridyl)imidazole;

1-[2-(4-Morpholinyl)ethyl]-4-(4-fluorophenyl)-5-(4-pyridyl)imidazole;

1-[3-(4-Morpholinyl)propyl]-4-(3-methylthiophenyl)-5-(4-pyridyl)imidazole;

(±)-1-[3-(4-Morpholinyl)propyl]-4-(3-methylsulfinylphenyl)-5-(4-pyridyl)imidazole;
1-[3-(N-methyl-N-benzyl)aminopropyl]-4-(3-methylthiophenyl)-5-(4-pyridyl)imidazole;
1-[3-(N-methyl-N-benzyl)aminopropyl]-4-(3-methylsulfinylphenyl)-5-(4-pyridyl)imidazole;
1-[4-(Methylthio)phenyl]-4-(4-fluorophenyl)-5-(4-pyridyl)imidazole;
1-[4(Methylsulfinyl)phenyl]-4-(4-fluorophenyl)-5-(4-pyridyl)imidazole;
1-[3-(Methylthio)phenyl]-4-(4-fluorophenyl)-5-(4-pyridyl)imidazole;
(±)-1-[3-(Methylsulfinyl)phenyl]-4-(4-fluorophenyl)-5-(4-pyridyl)imidazole;
1-[2-(Methylthio)phenyl]-4-(4-fluorophenyl)-5-(4-pyridyl)imidazole;
1-[2-(Methylsulfinyl)phenyl]-4-(4-fluorophenyl)-5-(4-pyridyl)imidazole;
1-[4-(4-Morpholinyl)butyl]-4-(4-fluorophenyl)-5-(4-pyridyl)imidazole;
1-Cyclopropyl-4-(4-fluorophenyl)-5-(4-pyridyl)imidazole;
1-Isopropyl-4-(4-fluorophenyl)-5-(4-pyridyl)imidazole;
1-Cyclopropylmethyl-4-(4-fluorophenyl)-5-(4-pyridyl)imidazole;
1-tert-Butyl-4-(4-fluorophenyl)-5-(4-pyridyl)imidazole;
1-(2,2-Diethoxyethyl)-4-(4-fluorophenyl)-5-(4-pyridyl)imidazole;
1-Formylmethyl-4-(4-fluorophenyl)-5-(4-pyridyl)imidazole;
1-Hydroxyiminylmethyl4-(4-fluorophenyl)-5-(4-pyridyl)imidazole;
1-Cyanomethyl-4-(4-fluorophenyl)-5-(4-pyridyl)imidazole;
1-3-(4-Morpholinyl)propyl)-4-(4-fluorophenyl)-5-(2-methylpyrid-4-yl)imidazole;
4-(4-Fluorophenyl)-1-[3-(4-morpholinyl)propyl]-5-(2-chloropyridin-4-yl) imidazole;
4-(4-Fluorophenyl)-1-[3-(4-morpholinyl)propyl]-5-(2-amino-4-pyridinyl) imidazole;
1-(4-Carboxymethyl)propyl-4-(4-fluorophenyl)-5-(4-pyridyl)imidazole;
1-(4-Carboxypropyl)4-(4-fluorophenyl)-5-(4-pyridyl)imidazole;
1-(3-Carboxymethyl)ethyl-4-(4-fluorophenyl)-5-(4-pyridyl)imidazole;
1-(3-Carboxy)ethyl-4-(4-fluorophenyl)-5-(4-pyridyl)imidazole;
1-(1-Benzylpiperidin-4-yl)-4-(4-fluorophenyl)-5-(4-pyridyl) imidazole;
5-(2-Aminopyrirnidin4-yl)-4-(4-fluorophenyl)-1-[3-(4-Morpholinyl)propyl]imidazole;
5-(2-Amninopyrimidin-4-yl)-4-(4-fluorophenyl)-1-(1-benzylpiperidin-4-yl)imidazole;
5-(2-Aminopyrimidin-4-yl)4(4-fluorophenyl)-1-(2-propyl)imidazole;
5-(2-Aminopyrimidin-4-yl)4-(4-fluorophenyl)-1-(cyclopropylmethyl)imidazole;
5-(2-Aniinopyrimidin4-yl)-4-(4-fluorophenyl)-1-(1-carboxyethyl-4-piperidinyl)imidazole;
5-(2-Aminopyrimidin-4-yl)4-(4-fluorophenyl)-1-(4-piperidinyl)imidazole;
1-Methyl-4-phenyl-5-(4-pyridyl)imidazole;
1-Methyl-4-[3-(cliorophenyl)]-5-[4-pyridinyl]imidazole;
1-Methyl-4-(3-methylthiophenyl)-5-(4-pyridyl)imidazole;
(±)-1-Methyl-4-(3-methylsulfinylphenyl)-5-(4-pyridyl)imidazole;
(±)4-(4-Fluorophenyl)-1-[3-(methylsulfinyl)propyl]-5-(4-pyridinyl)imidazole;
4-(4-Fluorophenyl)-1-[(3-methylsulfonyl)propyl]-5-(4-pyridinyl)imidazole;
1-(3-Phenoxypropyl)4(4-fluorophenyl)-5-(4-pyridinyl) imidazole;
1-[3-(Phenylthio)propyl]-4-(4-fluorophenyl)-5-(4-pyridiny)imidazole;
1-[3-(4-Morpholinyl)propyl-4-(4-fluorophenyl)-5-(4-quinolyl)imidazole;
(±)-1-(3-Phenylsulfinylpropyl)-4-(4-fluorophenyl)-5-(4-pyridinyl)imidazole;
1-(3-Ethoxypropyl)-4-(4-fluorophenyl)-5-(4-pyridinyl) imidazole;
1-(3-Phenylsulfonylpropyl-4-(4-fluorophenyl)-5-(4-pyridinyl)imidazole;
1-[3-(4-Morpholinyl)propyl]-4-(3-chlorophenyl)-5-(4-pyridyl)imidazole;
1-[3-(4-Morpholinyl)propyl]-4-(3,4-dichlorophenyl)-5-(4-pyridyl)imidazole;
4-[4-(Fluorophenyl)-1-[3-(4-morpholinyl)propyl]-5-(pyrimid-2-one-4-yl)imidazole;
4-(4-Fluorophenyl)-5-[2-(methylthio)-4-pyrirnidinyl]-1-[3-(4-morpholinyl)propyl]-imidazole;
(±)-(4-Fluorophenyl)-5-[2-(methylsulfinyl)-4-pyrimidinyl]-1-[3-(4-molpholinyl)-propyl]imidazole;
(E)-1-(1-Propenyl)-4-(4-fluorophenyl)-5-(4-pyridinyl) imidazole;
1-(2-Propenyl)-4-(4-fluorophenyl)-5-(4-pyridinyl) imidazole;
5-[(2-N,N-Dimethylamino)pyrimidin-4-yl]-4-(4-fluorophenyl)-1-[3-(4-morpholinyl)-propyl]imidazole;
1-[3-(4-Morpholinyl)propyl]-5-(4-pyridinyl)-4-[4-(trifluoromethyl)phenyl]imidazole;
1-[3-(4-Morpholinyl)propyl]-5-(4-pyridinyl)-4-[3-(trifluoromethyl)phenyl]imidazole;
1-(Cyclopropylmethyl)-4-(3,4-dichlorophenyl)-5-(4-pyridinyl)imidazole;
1-(Cyclopropylmethyl)-4-(3-trifluoromethylphenyl)-5-(4-pyridinyl)imidazole;
1-(Cyclopropylmethyl)-4-(4-fluorophenyl)-5-(2-methylpyrid-4-yl)imidazole;
1-[3-(4-Morpholinyl)propyl]-5-(4-pyridin[]yl)-4-(3,5-bistrifluoromethylphenlyl)- imidazole;
5-[4-(2-Aminopyrimidinyl)]-4-(4-fluorophenyl)-I-(2-carboxy-2,2-dimethylethyl)imidazole;
1-(1-Fornyl-4-piperidinyl)4-(4-fluorophenyl)-5-(4-pyridinyl)imidazole;
5-(2-Amino-4-pyrimidinyl)-4-(4-fluorophenyl)-1-(1-methyl-4-piperidinyl)imidazole;
1-(2,2-Dimethyl-3-morpholin-4-yl)propyl-4-(4-fluorophenyl)-5-(2-Amino-4-pyrimidinyl)imidazole;
4-(4-Fluorophenyl)-5-(4-pyridyl)-1-(2-acetoxyethyl) imidazole;
5-(2-Aminopyrimidin4-yl)-4-(4-fluorophenyl)-1-(1-benzylpyrrolin-3-yl)imidazole;
5-(2-Aminopyrimidin4-yl)-4-(4-fluorophenyl)-1-(2,2,6,6-tetramethylpiperidin4-yl)imidazole;
5-[4-(2-N-Methylamino)pyrimidinyl]-4-(4-fluorophenyl)-1-(4-N-methylpiperidine)-imidazole;
5-[4-(2-N-Methylamino)pyriniidinyl]-4-(4-fluorophenyl)-1-(4-N-morpholino-1-propyl)imidazole;
5-[4-(2-N-Methylamino)pyrimidinyl]-4-(4-fluorophenyl)-1-(4-piperidine)imidazole;
5-[(2-Ethylarnino)pyrimidin-4-yl]-4-(4-fluorophenyl)-1-(1-methylpiperdin-4-yl)-imidazole;
4-(4-Fluorophenyl)-5-[2-(isopropyl)arninopyrimidiny-4-yl]-1-(1-methylpiperdin-4-yl)imidazole;
5-(2-Acetamido-4-pyrimidinyl)-4-(4-fluorophenyl)-1-(4-N-morpholino-1-propyl)-imidazole;

5-(2-Acetamido-4-pyrimidinyl)-4-(4-fluorophenyl)- 1-(1-methyl-4-piperidinyl)- imidazole;
5-[4-(2-N-Methylthio)pyrimidinyl ]-4-(4-fluorophenyl)- 1-(4-piperidine)imidazole;
4-(Fluorophenyl)-1-(methyl-4-piperidinyl)-5-(2-methylthio-4-pyrimidinyl)imidazole;
4-(Fluorophenyl)- 1-(methyl-4-piperidinyl)-5-(2-methysulfinyl-4-pyrimidinyl)imidazole;
1-tert-Butyl-4-(4-fluorophenyl)-5-(2-methysulfinyl-4-pyrimidinyl)imidazole;
5-[4-(2-Aminopyrirnidinyl)]-4-(4-fluorophenyl)- 1-(2,2,6,6-tetramethyl-4-piperidinyl)imidazole;
5-[4-(2-N-Methylamino-4-pyriniidinyl)]-4-(4-fluorophenyl)- 1-(2,2,6,6-tetra-methyl- 4-piperidine)imidazole;
5-(2-Amino-4-pyrimidinyl)-4-(4-fluorophenyl)- 1-(tetrahydro-4-thiopyranyl)- imidazole;
5-(2-Arnino-4-pyrirnidinyl)-4-(4-fluorophenyl)-1-(tetrahydrowpyranyl)imidazole;
5-(2-Methylarnino-4-pyrimnidinyl)-4-(4-fluorophenyl)- 1-(2-cyanoethyl)imidazole;
5-(2-Amino-4-pyrimidinyl)-4-(4-fluorophenyl)-1-(tetrahydro-4-sulfinylpyranyl)- imidazole;
5-(2-Arnino-4-pyrifnidinyl)-4-(4-fluorophenyl)- 1-(tetrahydro-4-sulfonylpyranyl)- imidazole;
5-(2-Methylamino-4-pyrinidinyl)-4-(4-fluorophenyl)-1-(2,2,2-trifluoroethyl-4-piperidinyl)imidazole;
5-(2-Amino-4-pyrimidinyl)4-(4-fluorophenyl)- 1-(trifluoroacetyl-4-piperidinyl)- imidazole;
5-(4-Pyridyl)-4-(4-fluorophenyl)-1-(4-piperidinyl) imidazole;
5-(4-Pyridyl)4-(4-fluorophenyl)-1 -(1 -t-butoxy carbonyl-4-piperidinyl)imidazole;
5-(2-amino-4-pyrimidinyl)-4-(4-fluorophenyl)- 1 -(4-(1,3-dioxycyclopentyl)cyclohexyl) imidazole;
5-(2-amino-4-pyrimidinyl)-4-(4-fluorophenyl)-1-(4-ketocyclohexyl)imidazole;
5-(2-amino-4-pyrirnidinyl)-4-(4-fluorophenyl)-1-(4-cyclohexyl oxime) imidazole;
5-(2-amino-4-pyrimidinyl)-4-(4-fluorophenyl)-1-(4-cyclohexyl hydroxylamine) imidazole;
5-(2-amino-4-pyrimidinyl)-4-(4-fluorophenyl)- 1 -(trans-4-hydroxyurea) imidazole;
5-(2-arnino-4-pyrimidinyl)-4-(4-fluorophenyl)-1-(cis-4-hydroxyurea) imidazole;
5-(2-aniino-4-pyrmidinyl)-4-(4-fluorophenyl)- 1 -(4-hydroxycyclohexyl)imidazole;
5-[4-(2-N-methylamino)pyrimidinyl]-4-(4-fluorophenyl)- 1 -(4-ketocyclohexyl)- imidazole;
5-[4-(2-N-methylamino)pyriridinyl]-4-(4-fluorophenyl)-1-(trans-4-hydroxy- cyclohexyl)imidazole;
5-[4-(2-N-methylamino)pyrimidinyl]-4-(4-fluorophenyl)- 1 -(cis -4-hydroxy- cyclohexyl)imidazole;
5-[4-(2-N-Methylamino)pyrirnidinyl]-4-(4-fluorophenyl)- 1-[4-(cis-pyrrolidinyl)- cyclohexyl]imidazole;
5-[4-(2-N-methylamino)pyrirnidinyl]-4-(4-fluorophenyl)- 1-[4-(trans--1-pyrrolidinyl)- cyclohexyl]imidazole;
5-[4-(2-N-methylamino)pyrimidinyl]-4-(4-fluorophenyl)- 1 -(4-ethynyl-4-hydroxy- cyclohexyl)imidazole;
5-[4-(2-N-methylamino)pyrimidinyl]-4-(4-fluorophenyl)- 1-(4-( 1 -propynyl)-4-hydroxycyclohexyl)imidazole;
5-[4-(2-N-methylarino)pyrimidinyl]-4-(4-fluorophenyl)-1-(4-amino-4-methyl- cyclohexyl)imidazole;
5-[4-(2-N-methylamino)pyrimidinyl]-4-(4-fluorophenyl)-1-(4-acetamido-4-methyl- cyclohexyl)imidazole;
5-[4-(2-N-methylamino)pyrimidinyl]-4-(4-fluorophenyl)- 1 -(4-hydroxy-4-methyl- cyclohexyl)imidazole;

5-[4-(2-N-methylamino)pyrimidinyl]-4-(4-fluorophenyl)-1-(4-oxiranyl- cyclohexyl)imidazole;
5-[4-(2-N-Methylamino)pyrirnidinyl]-4-(4-fluorophenyl)- 1-(4-cyanomethyl-4-hydroxycyclohexyl)imidazole;
5-[4-(2-N-Methylamino)pyrimidinyl]-4-(4-fluorophenyl)- 1-(4-hydroxy4-hydroxymethylcyclohexly)imidazole;
5-[4-(2-Amino)pyrirnidinyl]-4-(4-fluorophenyl)- 1-[4-hydroxy-4-(1-propynyl)- cyclohexyl]imidazole;
5-[4-(2-Amino)pyrimidinyl]-4-(4-fluorophenyl)- 1 -(4-hydroxy-4-methyl- cyclohexyl)imidazole;
5-[4-(2-N-methylamino)pyrirnidinyll-4-(4-fluorophenyl)- 1 -(4-hydroxy-4-isopropyl- cyclohexyl)imidazole;
5-[4-(2-N-methylaniino)pyrinidinyl]-4-(4-fluorophenyl)-1-(4-hydroxy-4-phenyl- cyclohexyl)imidazole;
5-[4-(2-N-methylamino)pyrimidinyll-4-(4-fluorophenyl)- 1 -(4-hydroxy-4-benzyl- cyclohexyl)imidazole;
5-[4-(2-N-methylamino)pyrimidinyl]-4-(4-fluorophenyl)-1-(4-hydroxy-4-cyanomethyl cyclohexyl)imidazole;
5-[4-(2-N-methylamino)pyrimidinyl]-4-(4-fluorophenyl)- 1 -(4-hydroxy-4-(2-cyanoethyl)cyclohexyl)imidazole;
5-[4-(2-N-methylamino)pyrinidinyl]-4-(4-fluorophenyl)- 1 -(4-hydroxy-4-(2-aminoethyl)cyclohexyl)imidazole;
5-[4-(2-N-methylamino)pyrimidinyl]-4-(4-fluorophenyl)- 1 -(4-hydroxy-4-(2-nitroethyl)- cyclohexyl)imidazole;
5-[4-(2-N-methylamino)pyrimidinyl]-4-(4-fluorophenyl)- 1 -(4-hydroxymethyl-4-amino- cyclohexyl)imidazole;
5-[4-(2-N-methylamino)pyrimidinyl]4-(4-fluorophenyl)-1-(4-hydroxy-4-amino- cyclohexyl)imidazole;
5-[4-(2-N-methylamino)pyrimidinyl]-4-(4-fluorophenyl)-1-(4-amino- cyclohexyl)imidazole;
5-[4-(2-N-methylamino)pyriniidinyl]4-(4-fluorophenyl)- 1 -(4-hydroxy-4-thiomethyl cyclohexyl)imidazole;
5-[4(2-N-methylamino)pyrimidinyl]-4-(4-fluorophenyl)-1-(4-hydroxy-4-hydroxy methylcyclohexyl)imidazole;
5-[4-(2-N-methylaniino)pyrimidinyl]-4-(4-fluorophenyl)-1-(4-hydroxy-4-aminomethyl- cyclohexyl)imidazole;
5-[4-(2-amnino)pyriniidinyl]-4-(4-fluorophenyl)- 1 -(4-amino-4-methyl- cyclohexyl)imidazole;
5-[4-(2-anino)pyrirnidinyl]-4-(4-fluorophenyl)- 1-(4-hydroxy-4-methyl- cyclohexyl)imidazole;
5-[4-(2-amino)pyrimidinyl]-4-(4-fluorophenyl)- 1 -(4-oxiranyl-cyclohexyl)imidazole;
4-(Fluorophenyl)-1-(methyl-4-piperidinyl)-5-(2-methysulfinyl-4-pyrimidinyl)- imidazole;
4-(Fluorophenyl)- 1-(methyl-4-piperidinyl)-5-(2-methylthio-4-pyrimidinyl)imidazole;
5-[(2-Benzylamnino)pyrimidin-4-yl]-4-(4-fluorophenyl)- 1-(1 -methylpiperdin-4-yl)imidazole;
4-(4-Fluorophenyl)- 1-(1 -methylpiperdin-4-yl)-5-[2-(4-tetrahydrothio- pyranyl)aminopyrimidin-4-yl]imidazole;
4-(4-Fluorophenyl)-5-[(2-hydroxy)ethylamino]pyrimidiny-4-yl- 1-(1-methyl-piperdin- 4-yl)imidazole;
5-[(2-(3-Chlorobenzylamino)pyrimidin-4-yl]-4-(4-fluorophenyl)-1-(1-methyl-iperdin- 4-yl)imidazole;
5-[(2-(1-Naphthylmethylamino)pyrimidin-4-yl]-4-(4-fluorophenyl)- 1-(1-methylpiperdin-4-yl)imidazole;
5-[(2-(1 -Benzyl4-piperidinylamino)pyrimidin-4-yl]-4-(4-fluorophenyl)- 1-(1-methylpiperdin4-yl)imidazole;
4-(4-Fluorophenyl)- 1-(1 -methylpiperdin-4-yl)-5-[2-[3-(morpholino)propyl]-aminopyrimnidiny-4-yl]imidazole;
5-[2[(3-Bromophenyl)amino]pyrimidin-4-yl]-4-(4-fluorophenyl)- 1-(1 -methylpiperdin- 4-yl)imidazole;
5-[(2(Piperonylamino)pyrinidin4-yl]-4-(4-fluorophenyl)-1-(1-methylpiperdin4-yl)imidazole;
5-[(2-(4-Piperdinylamino)pyrimidin-4-yl]-4-(4-fluorophenyl)-1-(1-methylpiperdin-4-yl)imidazole;
5-[(2-(5-Chlorotryptamino)pyrimidin-4-yl]-4-(4-fluorophenyl)- 1-(1-methylpiperdin- 4-yl)imidazole;

5-[(2-(2,2,6,6-tetramethylpiperidin-4-yl)aminopyrimidin-4-yl]-4-(4-fluorophenyl)- 1-(1 -methylpiperdin-4-yl) imidazole;
5-[(2-[( 1-Ethoxycarbonyl)piperdin4-yljaminopyrimidin4-yl]-4-(4-fluorophenyl)-1-(1-methylpiperdin4yl) imidazole;
1-(4-Oxocyclohexyl)-4-(4-fluorophenyl)-5-[(2-methoxy) pyriadin-4-yl]imidazole;
cis - 1 -(4-Hydroxycyclohexyl)-4-(4-fluorophenyl)-5-[(2-methoxy)pyrimidin-4-yl]imidazole;
trans- 1-(4-Hydroxycyclohexyl)-4-(4-fluorophenyl)-5-[(2-methoxy)pyrimidin-4-yl]imidazole;
1-(4-Oxocyclohexyl)-4-(4-fluorophenyl)-5-[(2-methylthio) pyrimidin-4-yl]imidazole;
trans-1-(4-Hydroxycyclohexyl)-4-(4-fluorophenyl)-5-[(2-methylthio)pyrirnidin-4-yl]imidazole;
1-(4-Oxocyclohexyl)-4-(4-fluorophenyl)-5-[(2-hydroxy) pyriniidin-4-yl]imidazole;
1 -(4-Oxocyclohexy l) -4- (4-fluoropheny l)-5 - [(2 -is opropoxy )pyrim-idin-4-yl]imidazole ;
1-(4-Hydroxycyclohexyl)-4-(4-fluorophenyl)-5-[(2-isopropoxy)pyrirnidin1-4-yl]imidazole;
trans-1-(4-Hydroxy-4-methylcyclohexyl)-4-(4-fluorophenyl)-5-[(2-methoxy) pyrimidin-4-yl]imidazole;
cis-1-(4-Hydroxy-4-methylcyclohexyl)-4-(4-fluorophenyl)-S-[(2-methoxy)pyrimidin- 4-yl]imidazole;
trans-1-(4-Hydroxycyclohexyl)-4-(4-fluorophenyl)-5-[(2-ethoxy)pyrimidine-4-yl]imidazole;
1-(4-Piperidinyl)-4-(4-fluorophenyl)-S-(2-phenoxypyrimidin-4-yI)imidazole;
1-(4-piperidinyl)-4-(4-fluorophenyl) -5-(2-phenoxy-4-pyridinyl)imidazole;
1-(4-piperidinyl)-4-(4-fluorophenyl)-5-[-?-(4-methoxyphenoxy)-4-pyridinyl]imidazole;
1-(4-piperidinyl)-4-(4-fluorophenyl)-5-[2-(4-fluorophenoxy)-4-pyridinyl]imidazole;
1-(Piperidin-4-yl)-4-(4-fluorophenyl)-5- [2-(4-methoxyphenoxy)pyrimdin-4-yl]imidazole,
1-(Piperidin-4-yl)-4-(4-fluorophenyl)-5-[2-(4-fluorophenoxy)pyrimidin-4yl]-imidazole;
1-(Piperidin-4-yl)-4-(4-fluorophenyl)-5-[2-(4-aminocarbonylphenoxy)pyrimdin-4-yl]-imidazole;
1-(Piperidin-4-yl)-4-(4-fluorophenyl)-5-[2-(4-ethylphenoxy)pyrimidin-4-yl]imidazole;
1-(Piperidin-4-yl)(4-fluorophenyl)-5-[2-(4-benzyloxyphenoxy)pyrimidin-4-yl]-imidazole;
1-(Piperidin-4-yl)-4-(4-fluorophenyl)-5-[2-(4-cyanophenoxy)pyrimnidin-4-yl]imidazole;
1-(Piperidin-4-yl)-4-(4-fluorophenyl)-5-[2-(4-hydroxyphenoxy)pyrimidin-4-yl]imidazole;
1-(4-Hydroxycyclohexyl)-4-(4-fluorophenyl)-5-[2-(phenoxy)pyrimidin-4-yl]imidazole;
1-(Piperidin-4-yl)-4-(4-fluorophenyl)-5-[2-(2,6-dimethylphenoxy)pyridin-4-yl]imidazole;
1-(Piperidin-4-yl)-4-(4-fluorophenyl)-5-[2-(4-methylphenoxy)pyridin-4-yl]imidazole;
1-(Piperidin-4-yl)-4-(4-fluorophenyl)-5-[2-(4-chlorophenoxy)pyridin-4-yl]imidazole;
1-[3-(N-Morpholino)propyl]-4-(4-fluorophenyl)-5-[2-(phenoxy)pyrimnidin-4-yl]imidazole;
1-(Piperidin-4-yl)-4-(4-fluorophenyl)-5-[2-(3-methoxyphenoxy)pyrimidin-4-yl]imidazole;
1-(Piperidin-4-yl)-4-(4-fluorophenyl)-5-[2-(4-phenylphenoxy)pyrimnidin-4-yl]imidazole;
1-(Piperidin-4-yl)-4-(4-fluorophenyl)-5-[2-(4-phenoxyphenoxy)pyrimidin-4-yl]imidazole;
1-(Piperidin-4-yl)-4-(4-fluorophenyl)-5-[2-(3-hydroxyphenoxy)pyriniidin-4-yl]imidazole;
1-(3-(N-Morpholino)propyl)-4-(4-fluorophenyl)-5-[2-(4-fluorophenoxy)pyrimidin-4-yl]imidazole;
1-(Piperidin-4-yl)-4-(4-fluorophenyl)-5-[2-(2-hydroxyphenoxy)pyrimidin-4-yl]imidazole;
1-(Piperidin-4-yl)-4-(4-fluorophenyl)-5-[2-((3,4-methylenedioxy)phenoxy)pyrimidin-4-yl]imidazole;
1-(Piperidin-4-yl)-4-(4-fluorophenyl)-5-[2-(3-fluorophenoxy)pyrimnidin-4-yl]imidazole;
1-(Piperidin-4-yl)-4-(4-fluorophenyl)-5-[2-(2-fluorophenoxy)pyrimnidin-4-yl]imidazole;
1-(Piperidin-4-yl)-4-(4-fluorophenyl)-5-[2-(2-methoxyphenoxy)pyrimidin-4-yl]imidazole;
1-(Piperidin-4-yl)-4-(4-fluorophenyl)-5-[2-(3-trifloromethylphenoxy)pyrimidin-4-yl]imidazole;
1-(Piperidin-4-y)-4-(4-fluorophenyl)-5-[2-(3,4-difluorophenoxy)pyrimidin-4-yl]imidazole;
1-(Piperidin4-yl)-4-(4-fluorophenyl)-5-[2-(4-methylsulfonylphenoxy)pyrimidin-4-yl]imidazole;
1-(4-Piperidinyl)-4-(4-fluorophenyl)-5-(2-thiophenoxypyrimidin-4-yl)imidazole;
1-(4-Piperidinyl)-4-(4-fluorophenyl)-5-[2-(1-methyltetrazol-5-ylthio)pyridin-4-yl]imidazole;
5-[2-(2-Hydroxyethoxy)pyrirnidin-4-yl]-4-(4-fluorophenyl)-1-(4-oxocyclohexyl)- imidazole;
5-[2-(2-Hydroxyethoxy)pyrimidin4-yi)-4-(4-fluorophenyl)-1-(4hydroxy cyclohexyl)- imidazole;
5-[2-(2-tert-Butylamino)ethoxypyrimidin-4-yl]-4-(4-fluorophenyl)-1-(4-oxocyclohexyl)- imidazole;
5-[2-(2-tert-Butylamino)ethoxypyrimidin-4-yl]-4-(4-fluorophenyl)-1-(4-hydroxy- cyclohexyl)imidazole;
1-(4-Piperidinyl)-4-(4-Flourophenyl)-5-(2-isopropoxy-4-pyrimidinyl) imidazole;
1-(4-Piperidinyl)-4-(4-Fluorophenyl)-5-(2-methoxy4pyrimidinyl) imidazole;
5-(2-Hydroxy4-pyrimidinyl)4-(4-fluorophenyl)- 1-(4-piperidinyl)imidazole;
5-(2-Methoxy-4-pyridinyl)-4-(4-fluorophenyl)- 1 -(4-piperidinyl)imidazole;
5-(2-iso-Propoxy-4-pyridinyl)-4-(4-fluorophenyl) -1 -(4-piperidinyl)imidazole;
5-(2-Methylthio4-pyrirnidinyl)-4-(4-fluorophenyl)- 1 -(4-piperidinyl)imidazole;
5-(2-Methylthio-4-pyrimidinyl)-4-(4-fluorophenyl)-1-[(1-methyl-4-piperidinyl]imidazole;
5-(2-Ethoxy-4-pyrimidinyl)-4-(4-fluorophenyl)-1-(4-piperidinyl)imidazole; 1-(1-Ethylcarboxylpiperidin-4-yl)-3-(4-thiomethylphenyl)-5-[2-(thiomethyl)-pyrimnidin-4-yl]-imidazole;
1-( 1 -Ethylcarbonylpiperidine-4-yl)-4-(4-methylsulfinylphenyl)-5-[2-methylsulfinyl- pyrimidin4-yl]imidazole;

or pharmaceutically acceptable salts thereof.

METHODS OF TREATMENT

The compounds of Formula (I) or a pharmaceutically acceptable salt thereof can be used in the manufacture of a medicament for the prophylactic or therapeutic treatment of any disease state in a human, or other mammal, which is exacerbated or caused by a neurotramatic event, such as closed head injuries.

Compounds of Formula (I) are capable of inhibiting proinflammatory cytokines, such as IL-1, IL-6, IL-8 and TNF and are therefore of use in therapy. IL-1, IL-6, IL-8 and TNF affect a wide variety of cells and tissues and these cytokines, as well as other leukocyte-derived cytokines, are important and critical inflammatory mediators of a wide variety of disease states and conditions. The inhibition of these pro-inflammatory cytokines is of benefit in controlling, reducing and alleviating many of these disease states.

Accordingly, the present invention provides for method of treating a neurotraumatic disease, in a mammal in need thereof, which comprises administering to said mammal an effective amount of a CSAID™ cytokine suppresive compound, wherein the compound is an inhibitor of CSBP/p38/RK kinase. Preferably, the cytokine inhibitor is a compound of Formula (I), or a pharmaceutically acceptable salt thereof.

The discovery that the compounds of Formula (I) are inhibitors of cytokines, specifically IL-1, IL-6, IL-8 and TNF, and CNSP/p38 is based upon the effects of the compounds of Formulas (I) on the production of the IL-1, IL-8 and TNF in in vitro assays which are described herein, or based upon the kinase or binding assay for CBSP as also described herein.

As used herein, the term "inhibiting the production of IL-1 (IL-6, IL-8 or TNF)" refers to:

a) a decrease of excessive in vivo levels of the cytokine (IL-1, IL-6, IL-8 or TNF) in a human to normal or sub-normal levels by inhibition of the in vivo release of the cytokine by all cells, including but not limited to monocytes or macrophages;

b) a down regulation, at the genomic level, of excessive in vivo levels of the cytokine (IL-1, IL-6, IL-8 or TNF) in a human to normal or sub-normal levels;

c) a down regulation, by inhibition of the direct synthesis of the cytokine (IL-1, IL-6, IL-8 or TNF) as a postranslational event; or d) a down regulation, at the translational level, of excessive in vivo levels of the cytokine (IL-1, IL-6, IL-8 or TNF) in a human to normal or sub-normal levels.

As used herein, the term "cytokine interfering" or "cytokine suppressive amount" refers to an effective amount of a compound of Formula (1) which will cause a decrease in the in vivo levels of the cytokine to normal or sub-normal levels, when given to a patient for the prophylaxis or treatment of a disease state which is exacerbated by, or caused by, excessive or unregulated cytokine production.

A new member of the MAP kinase family, alternatively termed CSBP, p38, or RK, has been identified, See Lee et al., Nature, Vol. 300 n(72), 739–746 (1994). Activation of this novel protein kinase via dual phosphorylation has been observed in different cell systems upon stimulation by a wide spectrum of stimuli, such as physicochemical stress and treatment with lipopolysaccharide or proinflammatory cytokines such as interleukin-1 and tumor necrosis factor. The cytokine biosynthesis inhibitors, of the present invention, compounds of Formula (I), have been determined to be potent and selective inhibitors of CSBP/p38/RK kinase activity. These inhibitors are of aid in determining the signaling pathways involvement in inflammatory responses.

In order to use a compound of Formula (I) or a pharmaceutically acceptable salt thereof in therapy, it will normally be Formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenteraly or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0. 1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of Formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds of Formula (I), the daily oral dosage regimen will preferably be from about 0.1 to about 80 mg/kg of total body weight, preferably from about 0.2 to 30 mg/kg, more preferably from about 0.5 mg to 15 mg. The daily parenteral dosage regimen about 0.1 to about 80 mg/kg of total body weight, preferably from about 0.2 to about 30 mg/kg, and more preferably from about 0.5 mg to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

The invention will now be described by reference to the following biological examples which are merely illustrative and are not to be construed as a limitation of the scope of the present invention.

BIOLOGICAL EXAMPLES

The cytokine-inhibiting effects of compounds of the present invention were determined by the following in vitro assays:

Interleukin - 1 (IL-1)

Human peripheral blood monocytes were isolated and purified from either fresh blood preparations from volunteer donors, or from blood bank buffy coats, according to the procedure of Colotta et al, J Immunol, 132, 936 (1984). These monocytes ($1 \times 10^6$) were plated in 24-well plates at a concentration of 1–2 million/ml per well. The cells were allowed to adhere for 2 hours, after which time non-adherent cells were removed by gentle washing. Test compounds were then added to the cells for 1 h before the addition of lipopolysaccharide (50 ng/ml), and the cultures were incubated at 37° C. for an additional 24 h. At the end of this period, culture super-natants were removed and clarified of cells and all debris. Culture supernatants were then immediately assayed for IL-1 biological activity, either by the method of Simon et al., J. Immunol. Methods, 84, 85, (1985) (based on ability of IL-1 to stimulate a Interleukin 2 producing cell line (EL-4) to secrete IL-2, in concert with A23 187 ionophore) or the method of Lee et al., J. Immuno Therapy, 6 (1), 1–12 (1990) (ELISA assay). While not all compounds of Formula (I) have been shown tested, many of the exemplified compound have been shown to be inhibitors of in vitro IL-1 produced by human monocytes.

Tumour Necrosis Factor (TNF):

Human peripheral blood monocytes were isolated and purified from either blood bank buffy coats or plateletpheresis residues, according to the procedure of Colotta, R. et al., J immunol, 132(2), 936 (1984). The monocytes were plated at a density of $1 \times 10^6$ cells/ml medium/well in 24-well multi-dishes. The cells were allowed to adhere for 1 hour after which time the supernatant was aspirated and fresh medium (1 ml, RPMI-1640, Whitaker Biomedical Products, Whitaker, Calif.) containing 1% fetal calf serum plus penicillin and streptomycin (10 units/ml) added. The cells were incubated for 45 minutes in the presence or absence of a test compound at 1 nM-10 mM dose ranges (compounds were solubilized in dimethyl sulfoxide/ethanol, such that the fmal solvent concentration in the culture medium was 0.5% dimethyl sulfoxide/0.5% ethanol). Bacterial lipopolysaccharide (*E. coli* 055:B5 [LPS] from Sigma Chemicals Co.) was then added (100 ng/ml in 10 ml phosphate buffered saline) and cultures incubated for 16–18 hours at 37° C. in a 5% $CO_2$ incubator. At the end of the incubation period, culture supernatants were removed from the cells, centrifuged at 3000 rpm to remove cell debris. The supernatant was then assayed for TNF activity using either a radio-immuno or an ELISA assay, as described in WO 92/10190 and by Becker et al., J Immunol, 1991, 147, 4307. The compounds of Formula (I) have been shown to be inhibitors of in vitro TNF produced by human monocytes.

IL-1 and TNF inhibitory activity does not seem to correlate with the property of the compounds of Formula (I) in mediating arachidonic acid metabolism inhibition. Further the ability to inhibit production of prostaglandin and/or leukotriene synthesis, by nonsteroidal anti-inflammatory drugs with potent cyclooxygenase and/or lipoxygenase inhibitory activity does not mean that the compound will necessarily also inhibit TNF or IL-1 production, at non-toxic doses.

Interleukin -8 (IL-8):

Primary human umbilical cord endothelial cells (HUVEC) (Cell Systems, Kirland, Wash.) are maintained in culture medium supplemented with 15% fetal bovine serum and 1% CS-HBGF consisting of aFGF and heparin. The cells are then diluted 20-fold before being plated (250 $\mu$l) into gelating coated 96-well plates. Prior to use, culture medium are replaced with fresh medium (200 $\mu$l ). Buffer or test compound (25 $\mu$l, at concentrations between 1 and 10 $\mu$M) is then added to each well in quadruplicate wells and the plates incubated for 6 h in a humidified incubator at 37° C. in an atmosphere of 5% $CO_2$. At the end of the incubation period, supernatant is removed and assayed for IL-8 concentration using an IL-8 ELISA kit obtained from R&D Systems (Minneapolis, Minn.). All data is presented as mean value (ng/ml) of multiple samples based on the standard curve. $IC_{50}$'s where appropriate are generated by non-linear regression analysis.

Cytokine Specific Binding Protein Assay

A radiocompetitive binding assay was developed to provide a highly reproducible primary screen for structure-activity studies. This assay provides many advantages over the conventional bioassays which utilize freshly isolated human monocytes as a source of cytokines and ELISA assays to quantify them. Besides being a much more facile assay, the binding assay has been extensively validated to highly correlate with the results of the bioassay. A specific and reproducible cytokine inhibitor binding assay was developed using soluble cystosolic fraction from THP.1 cells and a radiolabeled compound. Patent application US Ser. No. 08/123175 Lee et al., filed September 1993, US Ser. No.; Lee et al., PCT 94/10529 filed Sep. 16, 1994 and Lee et al., Nature 300, n(72), 739–746 (December 1994) whose disclosures are incorporated by reference herein in its entirety describes the above noted method for screening drugs to identify compounds which interact with and bind to the cytokine specific binding protein (hereinafter CSBP). However, for purposes herein the binding protein may be in isolated form in solution, or in immobilized form, or may be genetically engineered to be expressed on the surface of recombinant host cells such as in phage display system or as fusion proteins. Alternatively, whole cells or cytosolic fractions comprising the CSBP may be employed in the creening protocol. Regardless of the form of the binding protein, a plurality of compounds are contacted with the binding protein under conditions sufficient to form a compound/binding protein complex and compound capable of forming, enhancing or interfering with said complexes are detected.

All exemplified compounds of Formula (I) have been shown as active, having an IC50<50 uM in this assay.

CSBP KINASE ASSAY:

This assay measures the CSBP-catalyzed transfer of $^{32}P$ from [a-$^{32}P$]ATP to threonine residue in an epidermal growth factor receptor (EGFR)-derived peptide (T669) with the following sequence: KRELVEPLTPSGEAPNQALLR (residues 661–681). (See Gallagher et al., "Regulation of Stress Induced Cytokine Production by Pyridinyl Imidazoles: Inhibition of CSPB Kinase", BioOrganic & Medicinal Chemistry, to be published 1996).

Kinase reactions (total volume 30 ul) contain: 25 mM Hepes buffer, pH 7.5; 10 mM $MgCl_2$; 170 uM ATP[1]; 10 uM Na ortho vanadate; 0.4 mM T669 peptide; and 20–80 ng of yeast-expressed purified CSBP2 (see Lee et al., Nature 300, n(72), 739–746 (December 1994)). Compounds (5 ul from [6X] stock[2]) are pre-incubated with the enzyme and peptide for 20 min on ice prior to starting the reactions with 32P/MgATP. Reactions are incubated at 30° C. for 10 min and stopped by adding 10 ul of 0.3 M phosphoric acid. 32P-labeled peptide is separated on phosphocellulose (Wattman, p81) filters by spotting 30 ul reaction mixture. Filters are washed 3 times with 75 mM phosphoric acid followed by 2 washes with $H_2O$, and counted for 32P.

[1] The Km of CSBP for ATP was determined to be 170 uM. Therefore, compounds screened at the Km value of ATP.

[2] Compounds are usually dissolved in DMSO and are diluted in 25 mM Hepes buffer to get final concentration of DMSO of 0.17%.

A number of the exemplified compounds of Formula (I) specifically noted herein have been shown to be active in this assay.

TNF-$\alpha$ in Traumatic Brain Injury Assay

The present assay provides for examnination of the expression of tumor necrosis faxtor mRNA in specfic brain regions which follow experimentally induced lateral fluid-percussion traumatic brain injury (TBI) in rats. Adult Sprague-Dawley rats (n=42) were anesthetized with sodium pentobarbital (60 mg/kg, i.p.) and subjected to lateral fluid-percussion brain injury of moderate severity (2.4 atm.) centered over the left temporaparietal cortex (n=18), or "sham" treatment (anesthesia and surgery without injury, n=18). Animals were sacrificed by decapitation at 1, 6 and 24 hr. post injury, brains removed, and tissue samples of left (injured) parietal cortex (LC), corresponding area in the contralateral right cortex (RC), cortex adjacent to injured parietal cortex (LA), corresponding adjacent area in the right cortex (RA), left hippocampus (LH) and right hippocampus (RH) were prepared. Total RNA was isolated and Northern blot hybridization was performed and quantitated relative to an TNF-$\alpha$ positive control RNA (macrophage=100%). A marked increase of TNF-$\alpha$ mRNA expression was observed in LH (104±17% of positive control, p<0.05 compared with sham), LC (105±21%, p<0.05) and LA (69±8%, p<0.01) in the traumatized hemisphere 1 hr. following injury. An increased TNF-$\alpha$ mRNA expression was also observed in LH (46±8%, p<0.05), LC (30±3%, p<0.01) and LA (32±3%, p<0.01) at 6 hr. which resolved by 24 hr. following injury. In the contralateral hemisphere, expression of TNF-$\alpha$ mRNA was increased in RH (46±2%, p<0.01), RC (4±3%) and RA (22±8%) at 1 hr. and in RH (28±11%), RC (7±5%) and RA (26±6%, p<0.05) at 6 hr. but not at 24 hr. following injury. In sham (surgery without injury) or naive animals, no consistent changes in expression of TNF-$\alpha$ mRNA was observed in any of the 6 brain areas in either hemisphere at any times. These results indicate that following parasagittal fluid-percussion brain injury, the temporal expression of TNF-$\alpha$ mRNA is altered in specific brain regions, including those of the non-traumatized hemisphere. Since TNF-$\alpha$ is able to induce nerve growth factor (NGF) and stimulate the release of other cytokines from activated astrocytes, this post-traumatic alteration in gene expression of TNF-$\alpha$ plays an important role in both the acute and regenerative response to CNS trauma.

CNS Injury model for IL-$\beta$ mRNA

This assay characterizes the regional expression of interleukin-1$\beta$ (IL-1$\beta$) mRNA in specific brain regions following experimental lateral fluid-percussion traumatic brain injury (TBI) in rats. Adult Sprague-Dawley rats (n=42) were anesthetized with sodium pentobarbital (60 mg/kg, i.p.) and subjected to lateral fluid-percussion brain injury of moderate severity (2.4 atm.) centered over the left temporaparietal cortex (n=18), or "sham" treatment (anesthesia and surgery without injury). Animals were sacrificed at 1, 6 and 24 hr. post injury, brains removed, and tissue samples of left (injured) parietal cortex (LC), corresponding area in the contralateral right cortex (RC), cortex adjacent to injured parietal cortex (LA), corresponding adjacent area in the right cortex (RA), left hippocampus (LH) and right hippocampus (RH) were prepared. Total RNA was isolated and Northern blot hybridization was performed and the quantity of brain tissue IL-1β mRNA is presented as percent relative radioactivity of IL-1β positive macrophage RNA which was loaded on same gel. At 1 hr. following brain injury, a marked and significant increase in expression of IL-1β mRNA was observed in LC (20.0±0.7% of positive control, n=6, p<0.05 compared with sham animal), LH (24.5±0.9%, p<0.05) and LA (21.5±3.1%, p<0.05) in the injured hemisphere, which remained elevated up to 6 hr. post injury in the LC (4.0±0.4%, n=6, p<0.05) and LH (5.0±1.3%, p<0.05). In sham or naive animals, no expression of IL-1β mRNA was observed in any of the respective brain areas. These results indicate that following TBI, the temporal expression of IL-1β mRNA is regionally stimulated in specific brain regions. These regional changes in cytokines, such as IL-1β play a role in the post-traumatic pathologic or regenerative seqtielae of brain injury.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows:

What is claimed is:

1. A method of treating a CNS injury to the brain caused by surgery, an open head injury, or a closed head injury in a mammal in need of such treatment, which method comprises administering to said mammal an effective amount of a compound of Formula (I), wherein:

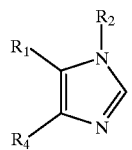

(I)

$R_1$ is 4-pyridyl, pyrimidinyl, quinolyl, isoquinolinyl, quinazolin-4-yl, 1-imidazolyl or 1-benzimidazolyl ring, which ring is optionally substituted independently one to three times with optionally substituted $C_{1-4}$ alkyl, halogen, hydroxyl, optionally substituted $C_{1-4}$ alkoxy, optionally substituted $C_{1-4}$ alkylthio, $C_{1-4}$ alkylsulfinyl, $CH_2OR_{12}$, amino, mono and di- $C_{1-6}$ alkyl substituted amino, or $N(R_{10})C(O)R_b$;

$R_4$ is phenyl, naphth-1-yl or naphth-2-yl, or a heteroaryl, which is optionally substituted by one or two substituents, each of which is independently selected, and which, for a 4-phenyl, 4-naphth-1-yl, 5-naphth-2-yl or 6-naphth-2-yl substituent, is halogen, cyano, nitro, —C(Z)NR_7R_{17}, C(Z)OR_{16}, —(CR_{10}R_{20})_vCOR_{12}, —SR_5, —SOR_5, —OR_{12}, halo-substituted-$C_{1-4}$ alkyl, $C_{1-4}$ alkyl, ZC(Z)R_{12}, —NR_{10}C(Z)R_{16}, or (CR_{10}R_{20})_v NR_{10}R_{20} and which, for other positions of substitution, is halogen, cyano, —C(Z)NR_{13}R_{14}, —C(Z)OR_3, —(CR_{10}R_{20})_m"COR_3, —S(O)_mR_3, —OR_3, halo-substituted-$C_{1-4}$ alkyl, —$C_{1-4}$ alkyl, —(CR_{10}R_{20})_m"NR_{10}C(Z)R_3, —NR_{10}S(O)_m'R_8, NR_{10}S(O)_m'NR_7R_{17}, —ZC(Z)R_3 or —(CR_{10}R_{20})_m"NR_{13}R_{14};

v is 0, or an integer having a value of 1 or 2;

m is 0, or the integer 1 or 2;

m' is an integer having a value of 1 or 2, m" is 0, or an integer having a value of 1 to 5;

$R_2$ is $C_{1-10}$ alkyl $N_3$, —(CR_{10}R_{20})_n'OR_9, heterocyclyl, heterocyclyl$C_{1-10}$ alkyl, $C_{1-10}$alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$ cycloalkenyl $C_{1-10}$alkyl, aryl, aryl$C_{1-10}$ alkyl, heteroaryl, heteroaryl $C_{1-10}$alkyl, (CR_{10}R_{20})_nOR_{11}, (CR_{10}R_{20})_nS(O)_mR_{18}, (CR_{10}R_{20})_n NHS(O)2R_{18}, (CR_{10}R_{20})_nNR_{13}R_{14}, (CR_{10}R_{20})_nNO_2, (CR_{10}R_{20})_nCN, (CR_{10}R_{20})_n'SO_2R_{18}, (CR_{10}R_{20})_nS(O)_m'NR_{13}R_{14}, (CR_{10}R_{20})_nC(Z)R_{11}, (CR_{10}R_{20})_nOC(Z)R_{11}, (CR_{10}R_{20})_nC(Z)OR_{11}, (CR_{10}R_{20})_nC(Z)NR_{13}R_{14}, (CR_{10}R_{20})_nC(Z)NR_{11}OR_9, (CR_{10}R_{20})_nNR_{10}C(Z)R_{11}, (CR_{10}R_{20})_nNR_{10}C(Z)NR_{13}R_{14}, (CR_{10}R_{20})_nN(OR_6)C(Z)NR_{13}R_{14}, (CR_{10}R_{20})_nN(OR_6)C(Z)R_{11}, (CR_{10}R_{20})_n C(=NOR_6)R_{11}, (CR_{10}R_{20})_nNR_{10}C(=NR_{19}) NR_{13}R_{14}, (CR_{10}R_{20})_nOC(Z)NR_{13}R_{14}, (CR_{10}R_{20})_n NR_{10}C(Z)NR_{13}R_{14}, (CR_{10}R_{20})_nNR_{10}C(Z)OR_{10}, 5-(R_{18})-1,2,4-oxadiazol-3-yl or 4-(R_{12})-5-(R_{18}R_{19})-4,5-dihydro-1,2,4-oxadiazol-3-yl; wherein the cycloalkyl, cycloalkylalkyl, aryl, arylalkyl, heteroaryl, heteroaryl alkyl, heterocyclic and heterocyclic alkyl groups may be optionally substituted;

n is an integer having a value of 1 to 10;

n' is 0, or an integer having a value of 1 to 10;

Z is oxygen or sulfur;

$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl;

$R_3$ is heterocyclyl, heterocyclyl$C_{1-10}$ alkyl or $R_8$;

$R_5$ is hydrogen, $C_{1-4}$ alkyl, $C_{2-4}$ alkenyl, $C_{2-4}$ alkynyl or $NR_7R_{17}$, excluding the moieties—$SR_5$ being —$SNR_7R_{17}$ and —$SOR_5$ being —SOH;

$R_6$ is hydrogen, a pharmaceutically acceptable cation, $C_{1-10}$ alkyl, $C_{3-7}$ cycloalkyl, aryl, aryl$C_{1-4}$ alkyl, heteroaryl, heteroaryl$C_{1-4}$ alkyl, heterocyclic, aroyl, or $C_{1-10}$ alkanoyl;

$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{15}$;

$R_8$ is $C_{1-10}$ alkyl, halo-substituted $C_{1-10}$ alkyl, $C_{2-10}$ alkenyl, $C_{2-10}$ alkynyl, $C_{3-7}$ cycloaLkyl, $C_{5-7}$ cycloalkenyl, aryl, aryl$C_{1-10}$ alkyl, heteroaryl, heteroaryl$C_{1-10}$ alkyl, (CR_{10}R_{20})_nOR_{11}, (CR_{10}R_{20})_nS (O)_mR_{18}, (CR_{10}R_{20})_nNHS(O)_2R_{18}, (CR_{10}R_{20})_n NR_{13}R_{14}; wherein the aryl, arylalkyl, heteroaryl, heteroaryl alkyl may be optionally substituted;

$R_9$ is hydrogen, —C(Z)$R_{11}$ or optionally substituted $C_{1-10}$ alkyl, $S(O)_2R_{18}$, optionally substituted aryl or optionally substituted aryl-$C_{1-4}$ alkyl;

$R_{10}$ and $R_{20}$ is each independently selected from hydrogen or $C_{1-4}$ alkyl;

$R_{11}$ is hydrogen, $C_{1-10}$ alkyl, $C_{3-7}$ cycloalkyl, heterocyclyl, heterocyclyl $C_{1-10}$ alkyl, aryl, aryl$C_{1-10}$ alkyl, heteroaryl or heteroaryl$C_{1-10}$ alkyl;

$R_{12}$ is hydrogen or $R_{16}$;

$R_{13}$ and $R_{14}$ is each independently selected from hydrogen or optionally substituted $C_{1-4}$ alkyl, optionally substituted aryl or optionally substituted aryl-$C_{1-4}$ alkyl, or together with the nitrogen to which they are attached form a heterocyclic ring of 5 to 7 members which ring optionally contains an additional heteroatom selected from oxygen, sulfur or $NR_9$;

$R_{15}$ is $R_{10}$ or $C(Z)$-$C_{1-4}$ alkyl;

$R_{16}$ is $C_{1-4}$ alkyl, halo-substituted-$C_{1-4}$ alkyl, or $C_{3-7}$ cycloalkyl;

$R_{18}$ is $C_{1-10}$ alkyl, $C_{3-7}$ cycloalkyl, heterocyclyl, aryl, arylalkyl, heterocyclyl, heterocyclyl-$C_{1-10}$alkyl, heteroaryl or heteroarylalkyl;

$R_{19}$ is hydrogen, cyano, $C_{1-4}$ alkyl, $C_{3-7}$ cycloalkyl or aryl; or a pharmaceutically acceptable salt thereof.

2. The method according to claim 1 wherein the compound is:

5-(4-Pyridyl)-4-(4-fluorophenyl)-1-(4-piperidinyl) imidazole;

or a pharmaceutically acceptable salt thereof.

3. The method according to claim 1 wherein $R_1$ is an optionally substituted 4-pyridyl.

4. The method according to claim 3 wherein the substituents are amino, or alkoxy.

5. The method according to claim 1 wherein $R_4$ is an optionally substituted phenyl.

6. The method according to claim 1 wherein $R_2$ is selected from optionally substituted heterocylcyl, optionally substituted heterocyclyl$C_{1-10}$ alkyl, $(CR_{10}R_{20})_n NS(O)_2 R_{18}$, $(CR_{10}R_{20})_n S(O)_m R_{18}$, aryl$C_{1-10}$ alkyl, $(CR_{10}R_{20})_n NR_{13}R_{14}$, optionally substituted $C_{3-7}$cycloalkyl, or optionally substituted $C_{3-7}$cycloalkyl $C_{1-10}$ alkyl.

7. The method according to claim 5 wherein $R_2$ is morpholino propyl, piperidine, N-methylpiperidine, N-benzylpiperidine, 2,2,6,6-tetramethylpiperidine, 4-aminopiperidine, 4-amino-2,2,6,6-tetramethyl piperidine, 4-hydroxycyclohexyl, 4-methyl-4-hydroxy cyclohexyl, 4-pyrrolinindyl-cyclohexyl, 4-methyl-4-aminocyclohexyl, 4-methyl-4-acetamidocyclohexyl, 4-keto cyclohexyl, 4-oxiranyl, or 4-hydroxy-4-(1-propynyl)cyclohexyl.

8. The method according to claim 5 wherein $R_1$ is an optionally substituted 4-pyrimindyl.

9. The method according to claim 8 wherein the substituents are amino or alkoxy.

10. The method according to claim 5 wherein the compound is:

cis -1-(4-Hydroxycyclohexyl)-4-(4-fluorophenyl)-5-[(2-methoxy)pyrimidin-4-yl]imidazole; or trans-1-(4-Hydroxycyclohexyl)-4-(4-fluorophenyl)-5-[(2-methoxy)pyrimidin-4-yl]imidazole;

or a pharmaceutically acceptable salt thereof.

11. The method according to claim 5 wherein the phenyl is substituted in the 4-position with fluoro, or substituted in the 3-position with fluoro, chloro, $C_{1-4}$ alkoxy, methanesulfonamido or acetamido, or the phenyl di-substituted at the 3,4-position independently with chloro or fluoro.

* * * * *